US00PP09882P

United States Patent [19]

Zaiger et al.

[11] Patent Number: Plant 9,882

[45] Date of Patent: May 6, 1997

[54] PEACH TREE SNOW BRIDE

[76] Inventors: Chris F. Zaiger, 929 Grimes Ave.; Leith M. Gardner, 1207 Grimes Ave.; Gary N. Zaiger, 1907 Elm Ave.; Grant G. Zaiger, 4005 California Ave., all of Modesto, Calif. 95358

[21] Appl. No.: 586,003

[22] Filed: Jan. 16, 1996

[51] Int. Cl.[6] ..... A01H 5/00

[52] U.S. Cl. ..... Plt./42.1

[58] Field of Search ..... Plt./42.1

*Primary Examiner*—James R. Feyrer

[57] ABSTRACT

A new and distinct variety of peach *Prunus persica*, tree, its novelty consists of the following unique combination of features that are desirable in a new variety:

1. Heavy and regular production of large size fruit.
2. Fruit with excellent flavor and eating quality.
3. Relatively uniform size of fruit throughout the tree.
4. Fruit with firm white flesh, good handling and shipping quality.
5. Fruit with a high degree of attractive red skin color.
6. Fruit holding firm on the tree 5 to 6 days after maturity (shipping ripe).
7. Vigorous, upright growth.

1 Drawing Sheet

ORIGIN OF THE VARIETY

The present new variety of peach tree was developed by us in our experimental orchard located near Modesto, Calif., as a second generation cross between two seedling selections with field identification numbers 22GA1110 and 16GA384. The maternal parent (22GA1110) originated from a cross between a nectarine seedling of unknown parentage and Redwing Peach (U.S. Plant Pat. No. #621). The pollen parent (16GA384) also originated from a cross between Redwing Peach and a nectarine seedling of unknown parentage. We grew and maintained a large group of these second generation seedlings under close observation, one such seedling, having especially desirable fruit characteristics, was selected for asexual reproduction and commercialization.

ASEXUAL REPRODUCTION OF THE VARIETY

The present new variety of peach tree was asexually propagated by budding, as performed by us in our experimental orchard, located near Modesto, Calif., and shows that all characteristics of the tree and its fruit are established and transmitted through succeeding asexual propagations and come true to the original tree in all respects.

SUMMARY OF THE VARIETY

The new and distinct variety of peach tree is of large size, vigorous, upright growth and a productive and regular bearer of large, firm, white flesh, clingstone fruit with excellent flavor and eating quality. The fruit is relatively uniform in size throughout the tree, holds firm on the tree 5 to 6 days after maturity (shipping ripe), has good handling and shipping quality and a high degree of attractive red skin color. In comparison to its white flesh parent Redwing Peach (U.S. Plant Pat. No. #621), the new variety has firmer flesh, with greater handling and shipping quality and a higher degree of attractive red skin color.

DESCRIPTION OF THE PHOTOGRAPH

The accompanying photographic illustration shows typical specimens of the foliage and fruit of the present new variety of peach tree. The upper and lower surface of the leaves are shown, also shown is an exterior and sectional view of the fruit being divided in the suture plane to show flesh coloration, pit cavity and a stone remaining in place.

The photographic illustration was taken shortly after being picked at maturity (firm ripe) and the colors are as nearly true as is reasonably possible in a color representation of this type.

DESCRIPTION OF THE VARIETY

The following detailed, botanical description of the new and distinct peach tree, its flowers, foliage and fruit are based on observations of specimens grown in our experimental orchard, located near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Productivity.*—Productive.
- *Bearing.*—Regular.

Trunk:
- *Size.*—Large.
- *Texture.*—Medium shaggy.
- *Color.*—Brown to soot brown (5–F–5) to (5–F–7).

Branches:
- *Size.*—Medium.
- *Texture.*—Smooth to medium rough, varies with age and growth.
- *Lenticels.*—Medium number. Large size.
- *Color.*—Light brown to brown (5–E–4) to (5–E–6).

Leaves:
- *Size.*—Large. Average length 7". Average width 1¾".
- *Form.*—Lanceolate, pointed.
- *Surface.*—Smooth.
- *Margin.*—Crenate.
- *Thickness.*—Medium.
- *Petiole.*—Medium length. Medium thickness.
- *Glands.*—Number varies from 1 to 4. Average number 2. Large size. Reniform. Located on upper portion of petiole and lower portion of leaf blade.
- *Color.*—Upper surface — green to dark green (28–F–6) to (28–F–8). Lower surface — grayish green to light green (28–E–6) to (28–E–8).

Flower buds:
- *Size.*—Medium.

*Length.*—Medium.
*Form.*—Plump.
*Pubescence.*—Pubescent.

Flowers:
*Size.*—Medium, non-showy.
*Blooming period.*—Date of first bloom: Mar. 2, 1994. Date of last bloom: Mar. 8, 1994. Varies slightly with climatic conditions.
*Pollen.*—Present.
*Color.*—Pink.

Fruit:
*Maturity when described.*—Firm ripe.
*Date of first picking.*—Jul. 22, 1994.
*Date of last picking.*—Jul. 28, 1994.
*Size.*—Large. Average diameter axially 3⅛". Average transversely in suture plane 3".
*Form.*—Nearly globose, slightly elongated.
*Suture.*—Shallow, extends from base to beyond the apex.
*Ventral surface.*—Varies from nearly round to very slightly lipped.
*Apex.*—Varies from round to slight pistil point.
*Base.*—Retuse.
*Cavity.*—Moderately rounded to elongated in suture plane. Average depth ½". Average breadth ⅞".

Flesh:
*Ripens.*—Evenly.
*Texture.*—Firm.
*Fibers.*—Few, small, tender.
*Juice.*—Moderate.
*Amygdalin.*—Undetected.
*Aroma.*—Moderate.
*Flavor.*—Excellent, mild, sweet, subacid.
*Eating quality.*—Excellent.
*Color.*—White to oyster shell white (1–A–1) to (1–A–2). Pit cavity — white to grayish white (2–A–2) to (2–B–3).

Skin:
*Thickness.*—Medium.
*Texture.*—Medium tough, tenacious to flesh.
*Tendency to crack.*—None.
*Down.*—Moderate, short in length.
*Color.*—White to yellowish white ground color (3–A–1) to (3–A–2). Overspread with Red to geranium red (11–B–7) to (11–B–8).

Stone:
*Type.*—Clingstone.
*Size.*—Large. Average length 1½". Average breadth 1 1/16". Average thickness ⅝".
*Form.*—Oval to ovoid.
*Base.*—Usually rounded varies from rounded to straight.
*Apex.*—Cuspidate.
*Sides.*—Equal to unequal.
*Surface.*—Irregularly furrowed toward apex, pitted toward base. Pit cavities vary from round to elongated.
*Ridges.*—Usually rounded.
*Tendency to split.*—None.
*Color.*—Brown to reddish brown (8–E–7) to (8–F–8).

Use: Dessert.
*Market.*—Local and long distance.

Keeping quality: Good.

Shipping quality: Good.

The present new variety of peach tree, its flowers, foliage and fruit, may vary is slight detail due to climate, soil conditions and cultural practices under which the variety may be grown. The present botanical description is that of the new variety grown under the ecological conditions prevailing near Modesto, Calif.

We claim:

1. A new and distinct variety of peach tree, substantially as illustrated and described, characterized by its large size, vigorous, upright growth and being a regular and productive bearer of large, white flesh, clingstone fruit with excellent flavor and eating quality; the fruit is further characterized by having firm flesh with good handling and shipping quality, having a high degree of attractive red skin color and in comparison to its white flesh parent Redwing Peach (U.S. Plant Pat. No. #621) the new variety has firmer flesh with greater handling and shipping quality and has a higher degree of attractive red skin color.

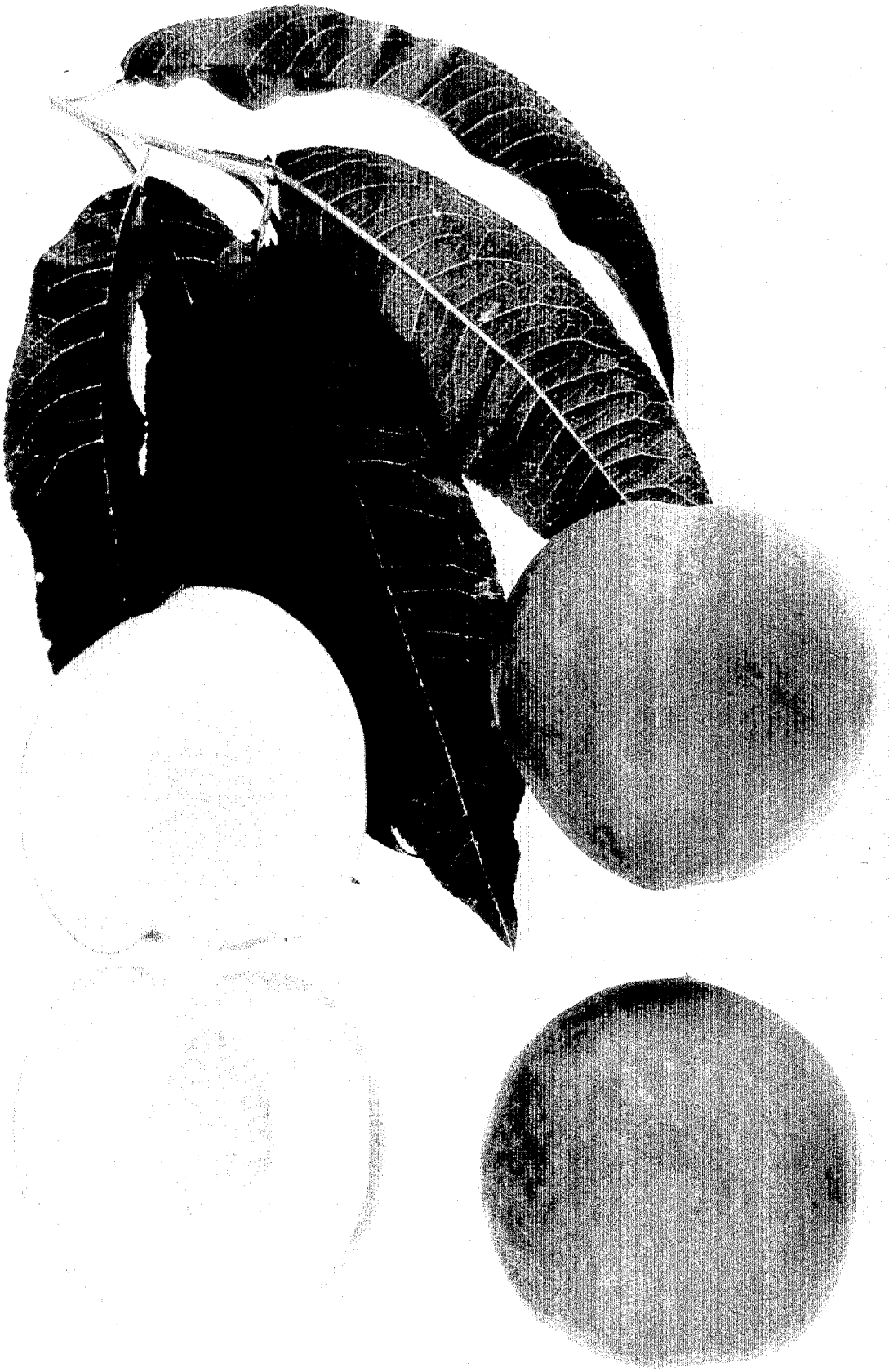

* * * * *